United States Patent
Thabuis et al.

(10) Patent No.: US 12,226,507 B2
(45) Date of Patent: Feb. 18, 2025

(54) USE OF DIANHYDROHEXITOL IN ORAL AND DENTAL CARE TO REDUCE THE DEVELOPMENT OF BACTERIAL STRAINS

(71) Applicant: ROQUETTE FRERES, Lestrem (FR)

(72) Inventors: Clémentine Thabuis, Ledringhem (FR); Caroline Perreau, La Couture (FR); Fabrice Desailly, Avion (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 16/764,711

(22) PCT Filed: Nov. 30, 2018

(86) PCT No.: PCT/FR2018/053059
§ 371 (c)(1),
(2) Date: May 15, 2020

(87) PCT Pub. No.: WO2019/106316
PCT Pub. Date: Jun. 6, 2019

(65) Prior Publication Data
US 2021/0169766 A1 Jun. 10, 2021

(30) Foreign Application Priority Data
Dec. 1, 2017 (FR) .................................. 1761521

(51) Int. Cl.
*A61K 8/49* (2006.01)
*A61Q 11/00* (2006.01)
*A61Q 17/00* (2006.01)

(52) U.S. Cl.
CPC ............ *A61K 8/4973* (2013.01); *A61Q 11/00* (2013.01); *A61Q 17/005* (2013.01); *A61K 2800/74* (2013.01)

(58) Field of Classification Search
CPC .................................. A61Q 11/00; A61K 7/16
USPC .................................................. 424/49, 401
See application file for complete search history.

(56) References Cited

U.S. PATENT DOCUMENTS

| | | | |
|---|---|---|---|
| 4,585,649 A * | 4/1986 | Lynch ................. | A61K 8/4973 424/49 |
| 4,627,979 A | 12/1986 | Lynch | |
| 7,049,299 B2 | 5/2006 | Francois | |
| 7,122,661 B2 | 10/2006 | Fleche et al. | |
| 8,008,477 B2 | 8/2011 | Fuertes | |
| 2008/0025926 A1 | 1/2008 | Kavouklis et al. | |
| 2008/0111269 A1* | 5/2008 | Politi .................. | A61K 9/2054 264/109 |
| 2018/0271765 A1* | 9/2018 | Gontarz ............... | A61K 8/20 |

FOREIGN PATENT DOCUMENTS

| | | | | |
|---|---|---|---|---|
| CN | 101829333 | * | 9/2010 | ............ A61K 47/32 |
| CN | 101829333 A | | 9/2010 | |
| WO | 2007045251 A2 | | 4/2007 | |
| WO | 2007063506 A2 | | 6/2007 | |
| WO | 2017106467 A1 | | 6/2017 | |

OTHER PUBLICATIONS

Roquette via Cosmetics Design Europe, "Isosorbide to fight bad breath by controlling oral pathogenic bacteria." www.cosmeticsdesign-europe.com. Published online Apr. 2019. (Year: 2019).*
Nayak et al., "The effect of xylitol on dental caries and oral flora." Clinical, Cosmetic and Investigational Dentistry 2014:6 89-94. (Year: 2014).*
Patil et al., "Oral Microbial Flora in Health." World Journal of Dentistry, Oct.-Dec. 2013;4(4);262-266. (Year: 2013).*
Hirata et al., "Antibacterial and anticariogenic properties of xylitol: a literature review." Brazilian Journal of Dentistry; 2018, p. 1-7. (Year: 2018).*
The English translation of the International Search Report, mailed on Mar. 21, 2019, in the corresponding PCT Appl. No. PCT/FR2018/053059.
"Practical Oral Microbiology", edited by Du Shenghui, Science and Technology Literature Publishing House, May 31, 2008. (5 pages).

* cited by examiner

Primary Examiner — Walter E Webb

(57) ABSTRACT

The invention relates to the non-therapeutic use of dianhydrohexitol to reduce the development of oral and dental bacterial strains.

15 Claims, 3 Drawing Sheets

Figure 1:
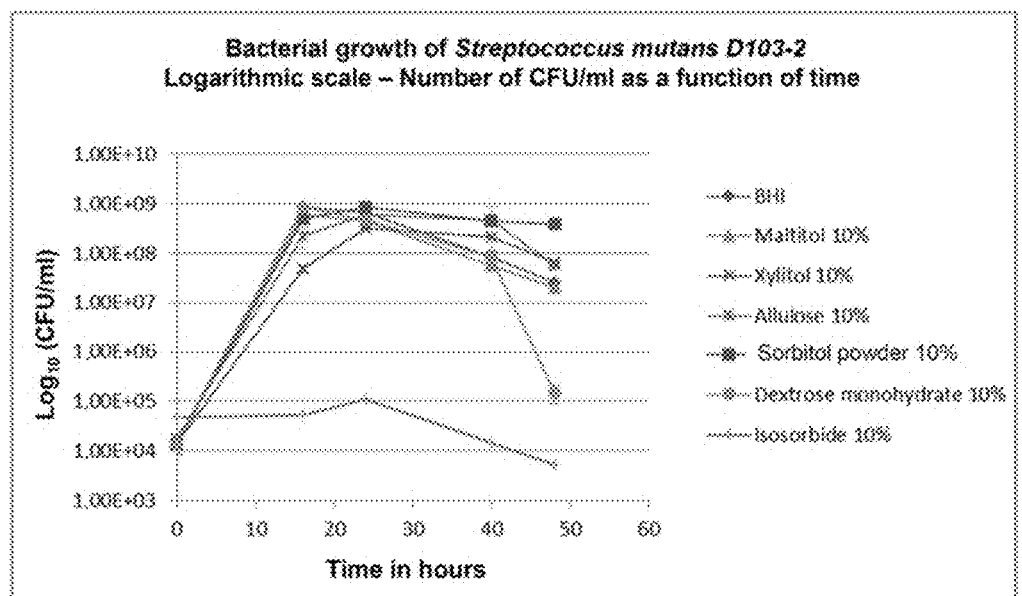

USE OF DIANHYDROHEXITOL IN ORAL AND DENTAL CARE TO REDUCE THE DEVELOPMENT OF BACTERIAL STRAINS

CROSS-REFERENCE TO RELATED APPLICATIONS

This application is a National Stage Application of PCT/FR2018/053059 filed Nov. 30, 2018, which claims priority from French Patent Application No. 1761521, filed on Dec. 1, 2017. The priority of said PCT and French Patent Application are claimed. Each of the prior mentioned applications is hereby incorporated by reference herein in its entirety.

TECHNOLOGICAL BACKGROUND AND FIELD OF APPLICATION

The present invention relates to the field of oral hygiene. It is notably directed toward the nontherapeutic use of dianhydrohexitol (1,4:3,6-dianhydrohexitol) as an agent for reducing the growth of oral bacterial strains. The dianhydrohexitol more particularly targeted in the present patent application is isosorbide.

In this regard, the effect of isosorbide on the growth of numerous oral bacterial strains is entirely surprising. Specifically, entirely unexpectedly, isosorbide leads to a particularly pronounced reduction in the growth of undesirable bacterial strains, in comparison with all the other polyols tested by the Applicant. Extremely surprisingly and advantageously, isosorbide offers a level of performance that is even higher than that observed with xylitol or sorbitol, which are the two polyols most commonly used in commercial toothpastes. This teaching is notably repeated in patent application WO 2003/007902, which recalls that these polyols are commonly used as humectant in toothpastes, making it possible notably to slow down the phenomenon of hardening of said paste. By way of example cited in said document, the product Neosorb 70/70 sold by the Applicant proves to be a polyol that is entirely efficient for the abovementioned purposes.

The Applicant indicates in the preamble that the dianhydrohexitols (1,4:3,6-dianhydrohexitols) targeted by the present invention are also known as isohexides, this name denoting products of internal dehydration of C6 hydrogenated sugars (hexitols) such as sorbitol, mannitol and iditol.

The oral hygiene field with which the present invention is concerned comprises any product, whether it is packaged as a liquid, a paste or a powder, which is directed toward preserving buccal health and improving oral health by preventing the appearance of infection or lesion in the buccal cavity. In particular, it may be a matter of toothpastes used notably in a recurrent manner during brushing of the teeth, mouthwashes which act on the entire buccal cavity and which may be used in a recurrent or occasional manner, or else local care products which may be, for example, in the form of a paste to be applied locally to a zone to be treated. This type of care product is generally directed more toward professional dentists than the general public, without, however, being limited thereto.

TECHNICAL PROBLEMS

Certain bacterial strains have a tendency to grow in the buccal cavity and may form a biofilm which, by growing on the tooth, will give rise to dental plaque. This film or this plaque may be formed on the tooth enamel, on a gum or on any supporting tissue of the buccal cavity. In the text hereinbelow, the term "supporting tissue" will denote without preference the support on which a bacterial strain has grown, whether it be the tooth enamel, a gum, a mucous membrane or another tissue of the buccal cavity.

The formation of a biofilm or of a plaque rapidly isolates the supporting tissue from the air, placing the supporting tissue and part of the film or plaque under anaerobic conditions. These anaerobic conditions may damage the supporting tissue and promote the growth of other bacterial strains, which are possibly more virulent.

In addition, the various bacterial strains are liable to generate harmful, chemically corrosive acids which have a demineralizing action on the teeth.

The activity of the biofilm or plaque combined with the anaerobic conditions imposed on the tissue may lead to rapid deterioration of the supporting tissue, which causes tooth decay, a lesion, inflammation or any other undesirable impairment of the supporting tissue.

It is thus desirable to reduce or prevent the growth of harmful bacterial strains in the buccal cavity. The main strains whose proliferation should be prevented are in particular *Streptococcus mutans*, *Lactobacillus gasseri*, *Actinomyces naeslundii*, and *Actinomyces oris*.

To this end, it is known practice to use antiseptic agents in order to reduce the amount of bacterial strains, or fluorinated compounds for forming a sparingly soluble protective layer on the tooth enamel.

However, these active compounds have adverse effects. In particular, these compounds are generally toxic—to varying degrees—and as such it is important to spit out the majority of oral hygiene products. The question of toxicity is particularly important in the case of children and infants since the toxic effects appear at lower doses than in the case of adults, and children and infants are more prone to accidentally swallow the product.

DESCRIPTION OF THE INVENTION

There is thus a need for a nontoxic compound for replacing the active agents of conventional oral hygiene products or, at least, to sufficiently reduce the content thereof without compromising the effect of these products.

The invention manages to satisfy this need by means of the nontherapeutic use of dianhydrohexitol for reducing the growth of oral bacterial strains.

The dianhydrohexitol is preferably isosorbide.

The effect of isosorbide on the growth of numerous oral bacterial strains is very surprising. Specifically, entirely unexpectedly, isosorbide leads to a particularly pronounced reduction in the growth of undesirable bacterial strains, in comparison with all the other polyols tested by the Applicant.

The bacteriostatic or even bactericidal effects of isosorbide are thus at the very least unexpected.

A subject of the invention is also a preventive or even therapeutic method for treating the buccal cavity, comprising the application of dianhydrohexitol, isosorbide being the preferred dianhydrohexitol, either to the buccal cavity or to a supporting tissue to be treated and which is subject to tooth decay, mouth ulcers, gingivitis or the like.

A subject of the invention is also an oral hygiene product comprising a dianhydrohexitol, isosorbide being the preferred dianhydrohexitol.

DETAILED DESCRIPTION OF THE INVENTION

In a more detailed manner, a first subject of the invention consists of the nontherapeutic use of dianhydrohexitol for reducing the growth of oral bacterial strains.

This use is also characterized in that the dianhydrohexitol may be used in a composition whose dianhydrohexitol content is at least 50% by weight, preferably at least 75%, even more preferably at least 90% and most preferably at least 95%.

This use is also characterized in that the dianhydrohexitol may be used together with at least one other polyol, preferentially chosen from glycerol, hydrogenated glucose syrups, maltitol, mannitol, sorbitol, erythritol, isomalt, lactitol and xylitol, and preferentially xylitol and maltitol and very preferentially xylitol. In this case, this at least one polyol may constitute the remainder to 100% by weight of said composition.

The term "dianhydrohexitol composition" denotes a formulation of at least two constituents, one of these constituents being a dianhydrohexitol, it being understood that this dianhydrohexitol is the major component in said formulation.

Preferably, said composition contains at least 50% by weight of said dianhydrohexitol, preferably at least 75%, even more preferably at least 90% and most preferably at least 95%.

According to one variant, said composition may consist of an aqueous solution of dianhydrohexitol, i.e. of water and of dianhydrohexitol and of other optional products in minor amount, for instance other polyols. Preferably, said aqueous solution contains only water and dianhydrohexitol, notably with at least 50% by weight of said dianhydrohexitol, preferably at least 75% and even more preferably about 80%.

According to another variant, said composition may consist of a paste, a powder or a product in flake or pellet form, predominantly composed of dianhydrohexitol.

In this regard, the Applicant indicates that, generally, dianhydrohexitols are synthesized in the presence of water (or water is generated during their synthesis): by recovering said dianhydrohexitol in this reaction medium, this immediately gives a composition in the form of an aqueous solution of dianhydrohexitol that may be used according to the invention. The dianhydrohexitol solutions may notably be obtained according to the processes described in the abovementioned patent applications EP 1 287 000 and WO 03/043959. It may be chosen to retain all or some of the water used during the preparation of the dianhydrohexitol or to eliminate all of the water to obtain a product in solid form, which will be returned into aqueous solution by simply adding water, which constitutes another possibility for preparing an aqueous solution of dianhydrohexitol that may be used according to the invention.

The aqueous solution in question may contain a single dianhydrohexitol, just as it may contain several thereof. These dianhydrohexitols (1,4:3,6-dianhydrohexitols) encompass isosorbide (1,4:3,6-dianhydrosorbitol), isomannide (1,4:3,6-dianhydromannitol), isoidide (1,4:3,6-dianhydroiditol) and mixtures of at least two of these products. Preferably, the aqueous solution contains only a single dianhydrohexitol, which is isosorbide.

Another subject of the present invention consists of an oral hygiene product comprising a dianhydrohexitol, preferably isosorbide. This hygiene product may be used preventively and daily, or curatively and in a limited manner over time.

The oral hygiene product according to the invention may notably comprise a dianhydrohexitol composition used according to the invention.

The oral hygiene product according to the invention may also comprise at least one other polyol, preferentially chosen from glycerol, hydrogenated glucose syrups, maltitol, mannitol, sorbitol, erythritol, isomalt, lactitol and xylitol, and preferentially xylitol and maltitol and very preferentially xylitol. It should be noted that the dianhydrohexitol composition can advantageously replace all or part of these polyols used in the formulation of oral hygiene products, due to the fact that it behaves intrinsically and just as efficiently as these polyols, as a humectant and water retainer.

According to a first variant, the oral hygiene product according to the invention may be a toothpaste. This toothpaste may be, for example, in the form of pastes or powders.

Alternatively, the oral hygiene product according to the invention may be a mouthwash, which is then generally in liquid form, ready to use or to be diluted.

Alternatively, the oral hygiene product according to the invention may be a local care product. Local care products comprise the care products used for treating gingivitis, mouth ulcers and oral wounds, in particular liquid dressings. In addition, for the purposes of the present invention, local care products comprise compositions applied by means of a dental floss, a gum or a wipe on which they are applied.

Preferably, the oral hygiene product according to the invention contains from 0.2% to 50% by weight, preferentially from 1% to 25% by weight and very preferentially from 5% to 15% by dry weight of dianhydrohexitol.

Preferably, the dianhydrohexitol (1,4:3,6-dianhydrohexitol) is chosen from isosorbide (1,4:3,6-dianhydrosorbitol), isomannide (1,4:3,6-dianhydromannitol), isoidide (1,4:3,6-dianhydroiditol) and mixtures of at least two of these products. Preferably, it is isosorbide.

The oral hygiene product according to the invention may also comprise a fluorinated compound, preferably a fluorinated compound chosen from sodium fluoride, sodium monofluorophosphate, tin fluoride or an amine fluoride. The combined use of a dianhydrohexitol, in particular of isosorbide, and of a fluorinated compound affords an increased bactericidal effect while at the same time making it possible to limit the amount of fluorinated compound and thus the overall toxicity of the oral hygiene product.

Moreover, it is known that an excess of fluorine can cause dental fluorosis, which is characterized by the appearance of marks on the teeth, especially in the case of children from 1 to 4 years old. The use of dianhydrohexitol, optionally combined with a polyol such as xylitol or maltitol, appears to be a solution for preventing the use of fluorinated compound and for preparing novel types of oral hygiene products that are healthier and safer to use, notably in the case of young children. As a result, a subject of the invention is also an oral hygiene product, comprising a dianhydrohexitol in particular such as isosorbide, optionally combined with a polyol in particular such as xylitol or maltitol, and free of fluorinated compound. This type of buccal hygiene product is particularly advantageous since it makes it possible to reduce both the risk of toxicity and the risk of appearance of white marks on the teeth of children and infants. It should be noted that the use of dianhydrohexitol, optionally combined with a polyol such as xylitol or maltitol, may take place by the buccal application of impregnated wipes.

The oral hygiene product according to the invention may also comprise an antiseptic agent, preferably chosen from chlorhexidine and 5-chloro-2-phenol. 5-Chloro-2-phenol is sometimes known as triclosan. The combined use of a dianhydrohexitol, in particular of isosorbide, and of an antiseptic agent affords an increased bactericidal effect while at the same time making it possible to limit the amount of antiseptic agent and thus the overall toxicity of the oral hygiene product. This is particularly true in the case of occasional-use mouthwashes, which use high concentrations of antiseptic agents. In one variant, the oral hygiene product according to the invention does not comprise any antiseptic agent; the dianhydrohexitol, and in particular the isosorbide, makes it possible to dispense with these potentially toxic antiseptic agents.

The oral hygiene product according to the invention may furthermore also comprise surfactants such as sodium lauryl sulfate. Sodium lauryl sulfate is a foaming agent which can increase the action of the oral hygiene product.

Figure 2:
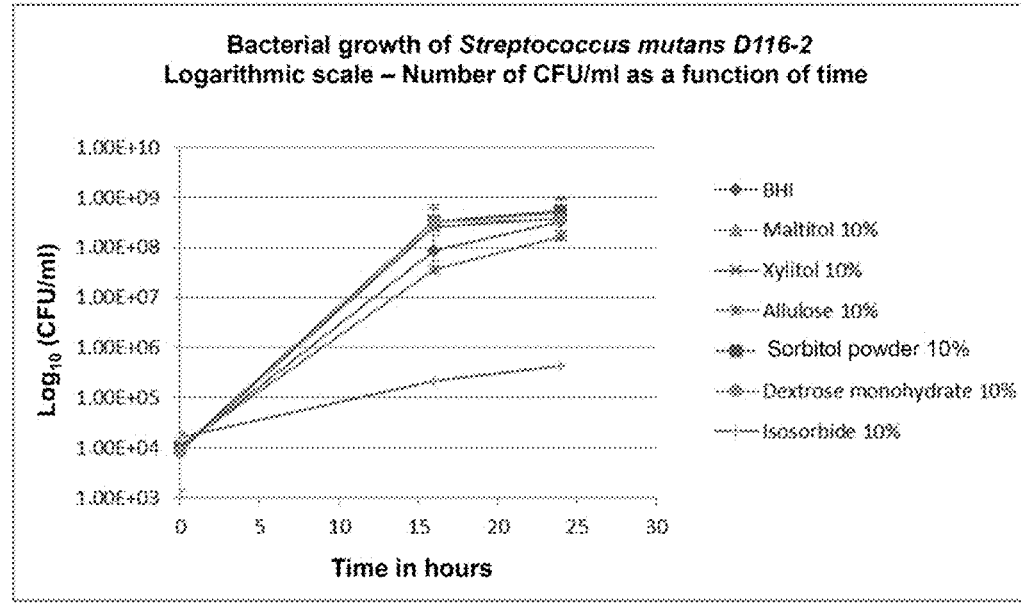
Figure 3:
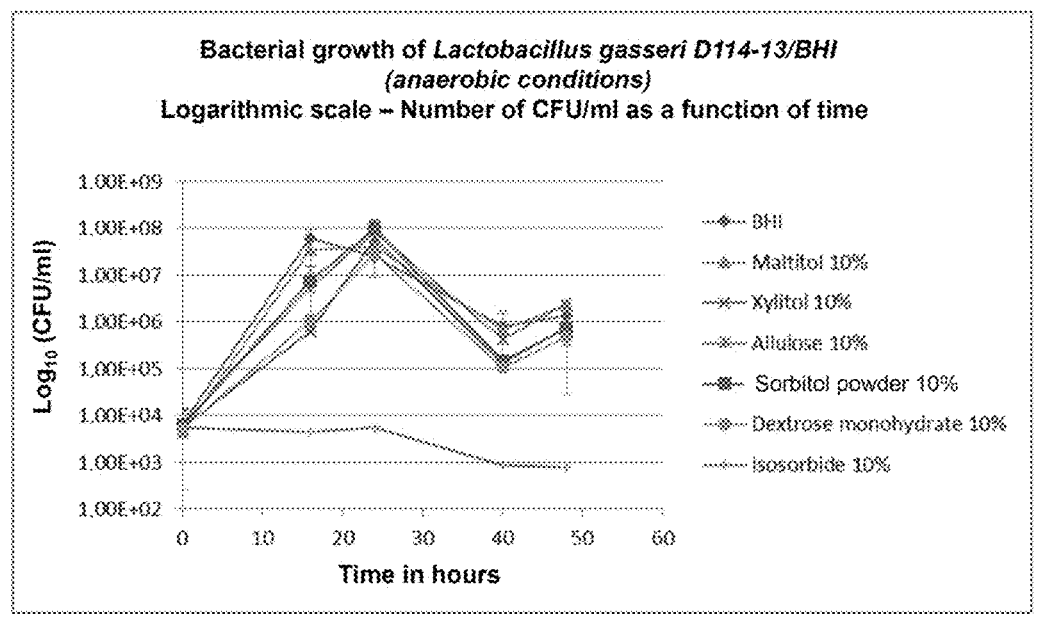
Figure 4:
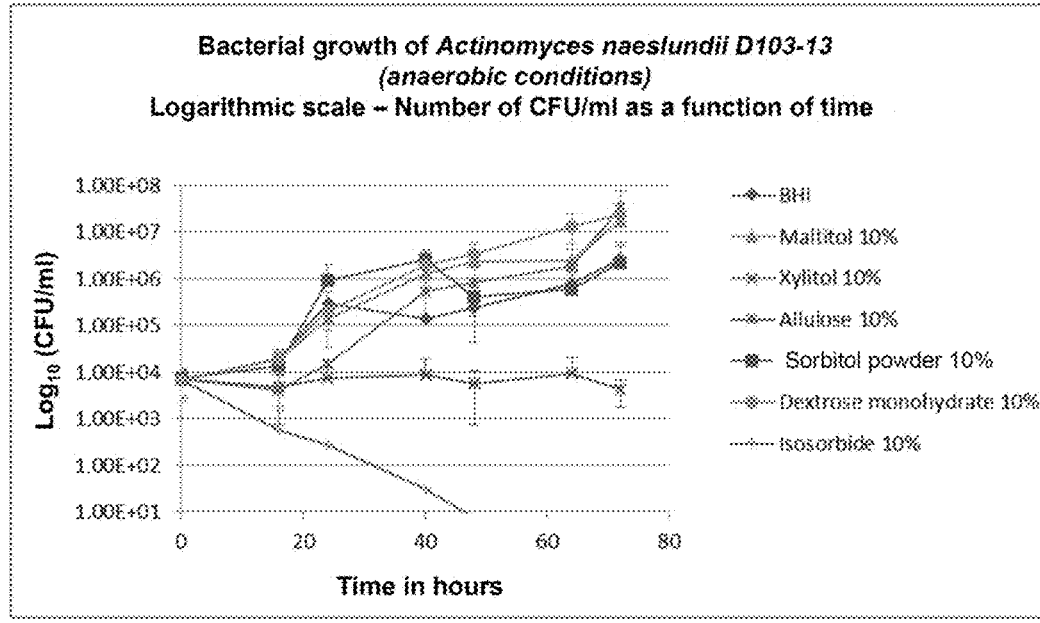
Figure 5:
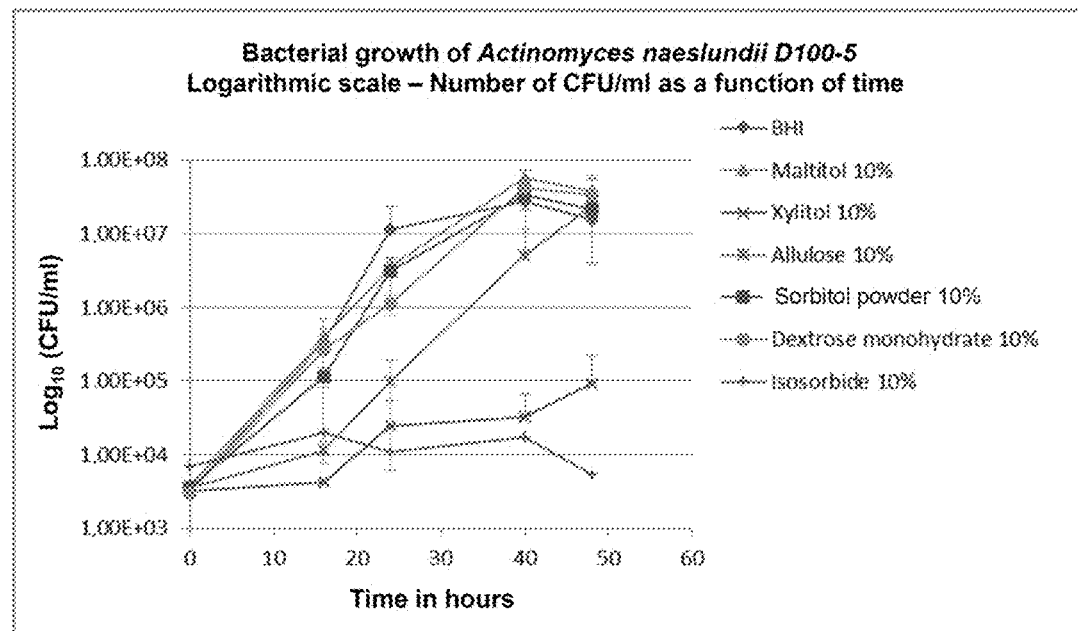
Figure 6:
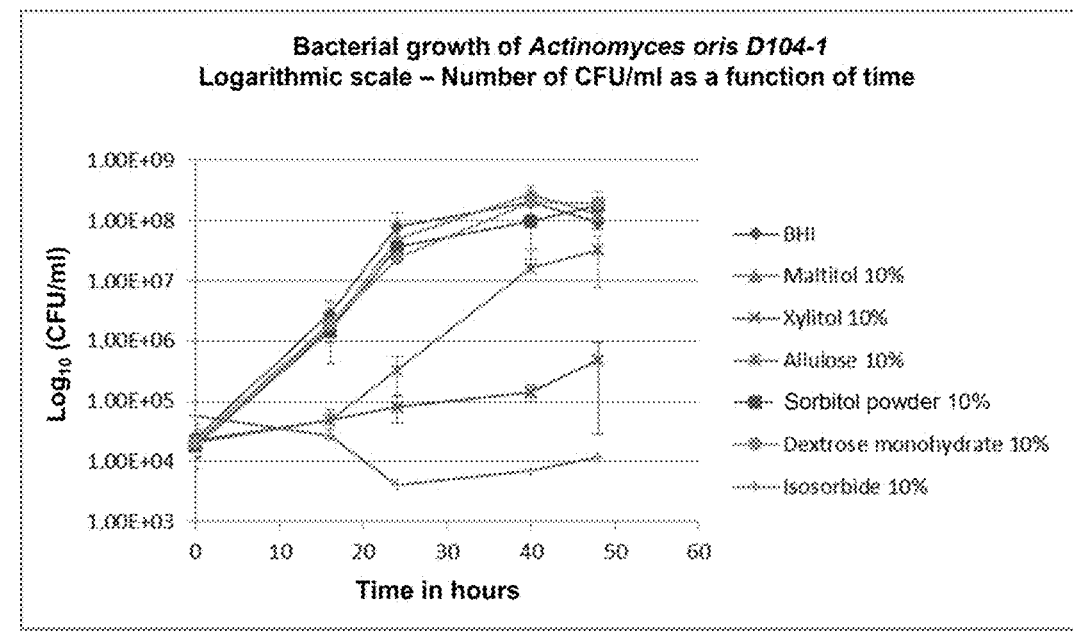

The invention may be better understood on reading the nonlimiting implementation examples described below and on examining the attached drawing, in which:

FIG. 1 shows the bacterial growth and the biofilm formed from a strain of Streptococcus mutans originating from a sample taken from a healthy tooth, under aerobic conditions, in the presence of various polyols, FIG. 2 shows the bacterial growth and the biofilm formed from a strain of Streptococcus mutans mutans originating from a sample taken from a decayed tooth, in the presence of various polyols, FIG. 3 shows the bacterial growth and the biofilm formed from a strain of Lactobacillus gasseri under anaerobic conditions, in the presence of various polyols, FIG. 4 shows the bacterial growth and the biofilm formed from a strain of Actinomyces naeslundii under aerobic conditions, in the presence of various polyols, FIG. 5 shows the bacterial growth and the biofilm formed from a strain of Actinomyces naeslundii under anaerobic conditions, in the presence of various polyols, and FIG. 6 shows the bacterial growth and the biofilm formed from a strain of Actinomyces oris under aerobic conditions, in the presence of various polyols.

The examples that follow consist in quantifying the action of various polyols on the growth of various bacterial strains that are liable to be found in the buccal cavity.

In order to demonstrate the effect of isosorbide on the growth of the main bacterial strains that grow in the oral environment, the four strains of interest were orally sampled: Streptococcus mutans, Lactobacillus gasseri, Actinomyces naeslundii and Actinomyces oris.

These strains were isolated and then identified in the bacteriology laboratory of the School of Pharmaceutical and Biological Sciences, Lille.

The growth of these strains was then measured in the presence of isosorbide, maltitol, xylitol, allulose, sorbitol powder and dextrose monohydrate in an unrefreshed culture medium, incubated at 37° C. for 48 hours or 72 hours under aerobic or anaerobic conditions.

The growths were measured by bacterial counting on solid medium.

The bacteria located at the surface, or at the time of formation of a plaque or of a film in the buccal cavity, grow in an aerobic environment, but once the plaque or the film has formed, the majority of the bacteria are in an anaerobic environment. It is thus interesting to evaluate the impact of the dianhydrohexitols, and in particular of the isosorbide, under both aerobic and anaerobic conditions.

The results are expressed in Log 10 (CFU/ml).

The culture media used are the Bacto Brain Heart Infusion (ref. 237500-BD (BHI)) and Difco™ Brain Heart Infusion Agar (ref. 241830-BD (BHIa)) culture media.

Streptococcus mutans (SM)

As illustrated in FIG. 1, under aerobic conditions and on a healthy tooth, at T=24 hours, the growths obtained with isosorbide remain absent. The population then declines slightly, revealing a bacteriostatic effect of isosorbide, in contrast with what is observed for all the other polyols tested.

Very slowed growth of the SMs is also observed on the strains originating from an oral sample taken from a decayed tooth, as illustrated in FIG. 2.

Under anaerobic conditions, as illustrated in FIG. 2, the bacterial growth varies little but the biofilm formed in the absence of isosorbide is much more pronounced than in the presence of isosorbide after 96 hours of incubation.

Lactobacillus gasseri

Lactobacillus gasseri only grows under anaerobic conditions. As illustrated in FIG. 3, at T=24 hours, the growth obtained with isosorbide remains absent, the populations declining beyond 24 hours, revealing an inhibitory effect of isosorbide that is not observed with the other polyols tested.

Actinomyces naeslundii

Under anaerobic conditions, as illustrated in FIG. 4, the bacterial population in the presence of isosorbide falls constantly until it disappears completely.

Isosorbide thus has a bactericidal effect.

The effect of xylitol will be noted: in the presence of xylitol, the bacterial population remains stable, whereas in the presence of the other polyols tested, the bacterial population undergoes exponential growth.

Under aerobic conditions, as illustrated in FIG. 5, the bacterial growth in the presence of isosorbide remains low relative to the other polyols. A substantial decrease in the bacterial population is observed from T=40 hours.

Again, xylitol appears to further curb the bacterial growth than the other polyols tested and, in fact, it may be advantageous to use it in combination with isosorbide.

Actinomyces oris

Under aerobic conditions, as illustrated in FIG. 6, the bacterial growth decreases greatly over time in the presence of isosorbide, then stabilizes after 24 hours.

In the presence of allulose and xylitol, the bacterial growth is slowed relative to the other polyols tested, but remains very much higher than that observed in the presence of isosorbide.

In all cases, a very significant decrease in the growth of the bacterial strains is thus observed in the presence of isosorbide. Such a result is particularly surprising, as there was nothing to suggest any particular behavior associated with isosorbide relative to the other polyols.

Extremely surprisingly and advantageously, isosorbide offers a level of performance that is even higher than that observed with xylitol or sorbitol, which are the polyols most commonly used in commercial toothpastes.

It is understood that the embodiments described are not limiting and that it is possible to provide further improvements to the invention without departing from the scope thereof.

Unless otherwise mentioned, the word "or" is equivalent to "and/or". Similarly, unless otherwise mentioned, the word "a(n)" or "one" is equivalent to "at least one".

The invention claimed is:

1. A method for reducing the growth of at least two harmful oral bacterial strains in the buccal cavity, comprising the step of administering an antibacterial agent consisting of a dianhydrohexitol in combination with xylitol, to one in need thereof, wherein the dianhydrohexitol is chosen from isosorbide (1,4:3,6-dianhydrosorbitol), isomannide (1,4:3,6-dianhydromannitol), isoidide (1,4:3,6-dianhydroiditol) and mixtures of at least two of these compounds.

2. The method as claimed in claim 1, wherein the dianhydrohexitol is in a composition whose dianhydrohexitol content is at least 50% by weight.

3. An oral hygiene product, comprising an antibacterial agent consisting of a dianhydrohexitol, in combination with xylitol, wherein the dianhydrohexitol is chosen from isosorbide (1,4:3,6-dianhydrosorbitol), isomannide (1,4:3,6-dianhydromannitol), isoidide (1,4:3,6-dianhydroiditol) and mixtures of at least two of these compounds.

4. The oral hygiene product as claimed in claim 3, further comprising at least one other polyol.

5. The oral hygiene product as claimed in claim 3, wherein the dianhydrohexitol content is between 0.2% and 50% by dry weight.

6. The oral hygiene product as claimed in claim 3, wherein the product is a toothpaste, or a mouthwash or a local care product.

7. The method as claimed in claim 1, wherein the bacterial strains are chosen from *Streptococcus mutans, Lactobacillus gasseri, Actinomyces naeslundii* and *Actinomyces oris*.

8. The method as claimed in claim 7, wherein the dianhydrohexitol is isosorbide.

9. The method as claimed in claim 1, wherein the dianhydrohexitol is in a composition whose dianhydrohexitol content is at least 75% by weight.

10. The oral hygiene product as claimed in claim 3, wherein the dianhydrohexitol is isosorbide.

11. The oral hygiene product as claimed in claim 4, wherein the polyol is chosen from glycerol, hydrogenated glucose syrups, maltitol, mannitol, sorbitol, erythritol, isomalt, lactitol and xylitol.

12. The oral hygiene product as claimed in claim 5, wherein the dianhydrohexitol content is between 1% to 25% by dry weight.

13. The oral hygiene product as claimed in claim 12 wherein the dianhydrohexitol content is between 5% to 15% by dry weight.

14. The method of claim 1, wherein the growth of oral bacterial strains is reduced in the one in need thereof.

15. A method for reducing the growth of at least two oral bacterial strains, comprising the step of administering the oral hygiene product as claimed in claim 5 to one in need thereof, thereby reducing the growth of oral bacterial strains in the one in need thereof.

* * * * *